US007255859B1

(12) United States Patent
Emrich et al.

(10) Patent No.: US 7,255,859 B1
(45) Date of Patent: Aug. 14, 2007

(54) MONOCLONAL ANTIBODIES AGAINST THE EPITOPE YPYDVPDYA, A PROCESS FOR THEIR PRODUCTION AND THEIR USE

(75) Inventors: Thomas Emrich, Iffeldorf (DE); Matthias Hinzpeter, Munich (DE); Michael Grol, Feldafing (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/284,787

(22) PCT Filed: Oct. 20, 1997

(86) PCT No.: PCT/EP97/05783

§ 371 (c)(1),
(2), (4) Date: Aug. 16, 1999

(87) PCT Pub. No.: WO98/17691

PCT Pub. Date: Apr. 30, 1998

(30) Foreign Application Priority Data

Oct. 21, 1996 (DE) ................................ 196 43 314

(51) Int. Cl.
*A61K 39/145* (2006.01)

(52) U.S. Cl. ............... 424/139.1; 424/93.2; 424/141.1; 424/186.1; 424/206.1; 435/346

(58) Field of Classification Search ................ 530/350, 530/387.1, 388.1, 388.2, 388.3; 435/326, 435/331, 339, 346, 347, 352, 353; 520/350, 520/387.1, 388.1, 388.2, 388.3; 424/93.2, 424/141.1, 139.1, 186.1, 206.1
See application file for complete search history.

(56) References Cited

FOREIGN PATENT DOCUMENTS

WO WO 92/09300 6/1992

OTHER PUBLICATIONS

Kuby (Immunology, Second Edition, W.H. Freeman and Company, 1994, pp. 160-164).*

Greenspan et al. (Nature Biotechnology 7: 936-937, 1999).*

Chen, et al., "Expression and localiztion of two low molecular weight GTP-binding proteins, Rab8 and Rab10, by epitope tag," Proc. Natl. Acad. Sci, USA, 90:6508-6512 (1993).

Field, et al., "Purification of a RAS-Responsive Adenylyl Cylase Complex from Saccharomyces cerevisiae by Use of an Epitope Addition Method," Molecular and Cellular Biology, 8:2159-2165 (1988).

Green, et al., "Immunogenic Structure on the Influenza Virus Hemagglutinin," Cell, 28:477-487 (1982).

Hinds, et al., "Synthesis, Conformational Properties, and Antibody Recognition of Peptides Containing Beta-Turn Mimetics Based on Alpha-Alkyproline Dervatives," Journal of Medicinal Chemistry,. 34:1777-1789 (1991).

Kolodziej, et al., "Epitope Tagging and Protein Surveillance," Biochemistry of Gene Expression, 194:508-519 (1991).

Wilson, et al., "The Structure of an Antigenic Determinant in a Protein," Cell, 37:767-778 (1984).

"Generation of Protein-Reactive Antibodies by Shon Peptides Is An Event of High Frequency: Implications for the Structural Basis of Immune Recognition," Niman et al., Proc. Natl. Acad. Sci., USA, vol. 80, Aug. 1983, pp. 4949-4953.

* cited by examiner

*Primary Examiner*—Robert A. Zeman
(74) *Attorney, Agent, or Firm*—Barnes & Thornburg LLP

(57) ABSTRACT

The invention concerns monoclonal antibodies against the epitope YPYDVPDYA (SEQ ID NO: 1) which is derived from the haemagglutinin of the human influenza virus and are suitable for the detection and isolation of native haemagglutinin of the human influenza virus, of modified haemagglutinin or of haemagglutinin fusion proteins and have an affinity of $>10^8$ $M^{-1}$, in particular of $10^9$ to $10^{10}$ $M^{-1}$.

6 Claims, 5 Drawing Sheets

Figure 1:
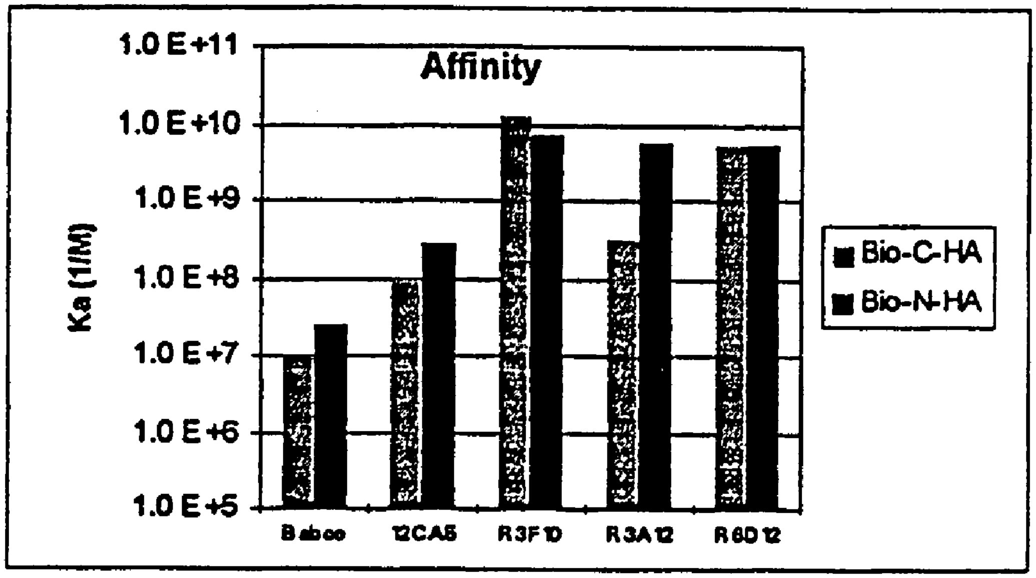

SEQUENCE LISTING

```
<160> NUMBER OF SEQ ID NOS: 5

<210> SEQ ID NO 1
<211> LENGTH: 9
<212> TYPE: PRT
<213> ORGANISM: human influenza virus

<400> SEQUENCE: 1

Tyr Pro Tyr Asp Val Pro Asp Tyr Ala
1               5


<210> SEQ ID NO 2
<211> LENGTH: 14
<212> TYPE: PRT
<213> ORGANISM: human influenza virus

<400> SEQUENCE: 2

Tyr Pro Tyr Asp Val Pro Asp Tyr Ala Gly Ser Gly Ser Lys
1               5                   10


<210> SEQ ID NO 3
<211> LENGTH: 13
<212> TYPE: PRT
<213> ORGANISM: human influenza virus
```

-continued

<400> SEQUENCE: 3

Ser Gly Ser Gly Tyr Pro Tyr Asp Val Pro Asp Tyr Ala
1 5 10

<210> SEQ ID NO 4
<211> LENGTH: 14
<212> TYPE: PRT
<213> ORGANISM: human influenza virus
<220> FEATURE:
<221> NAME/KEY: MISC_FEATURE
<222> LOCATION: (1)..(1)
<223> OTHER INFORMATION: acetyl group attached
<220> FEATURE:
<221> NAME/KEY: MISC_FEATURE
<222> LOCATION: (14)..(14)
<223> OTHER INFORMATION: (epsilon-biotinoyl)-amide group attached

<400> SEQUENCE: 4

Tyr Pro Tyr Asp Val Pro Asp Tyr Ala Gly Ser Gly Ser Lys
1 5 10

<210> SEQ ID NO 5
<211> LENGTH: 13
<212> TYPE: PRT
<213> ORGANISM: human influenza virus
<220> FEATURE:
<221> NAME/KEY: MISC_FEATURE
<222> LOCATION: (1)..(1)
<223> OTHER INFORMATION: (biotinoly-epsilon-Aca) group attached
<220> FEATURE:
<221> NAME/KEY: MISC_FEATURE
<222> LOCATION: (13)..(13)
<223> OTHER INFORMATION: amide group attached

<400> SEQUENCE: 5

Ser Gly Ser Gly Tyr Pro Tyr Asp Val Pro Asp Tyr Ala
1 5 10

MONOCLONAL ANTIBODIES AGAINST THE EPITOPE YPYDVPDYA, A PROCESS FOR THEIR PRODUCTION AND THEIR USE

The invention concerns monoclonal antibodies against the epitope YPYDVPDYA which is derived from the haemagglutinin of the human influenza virus and are suitable for the detection and isolation of native haemagglutinin from the human influenza virus, of modified haemagglutinin or of haemagglutinin fusion proteins and have an affinity of $>10^8$ $M^{-1}$, in particular of $10^9$ to $10^{10}$ $M^{-1}$.

Haemagglutinins are substances—usually glycoproteins—which have the ability to agglutinate erythrocytes. They occur among others as components of viruses such as e.g. in myxoviruses or pox viruses. The haemagglutinin (HA) of the influenza virus which is a membrane-coated virus with a (−) RNA genome is of particular importance. The influenza haemagglutinin is a transmembrane surface antigen which protrudes from the spherical lipid coat in the form of spikes which can be seen in electron-microscopic pictures. The HA spikes are trimers, the monomers of which are composed of two polypeptide chains, HA1 (46,000-65,000 D) and HA2 (21,000-30,000 D). The haemagglutinin in the membrane of the influenza virus enables the virus to penetrate into susceptible host cells e.g. of the respiratory tract.

It is known that antibodies against haemagglutinin are effective inhibitors of a viral infection. However, the specific affinity of the antibody does not generally apply to the whole macromolecular protein but only to a special epitope.

Nowadays the technique of epitope tagging, i.e. the attachment of an epitope to a protein by molecular biological techniques, is a method that is frequently used to analyse proteins and in principle is independent of the epitope used. In this method the primary sequence of an arbitrary protein is extended by a few amino acids with the aid of recombinant techniques. The decisive factor is only the presence of a specific and high affinity antibody with a known recognition sequence. Using antibodies that are specifically directed against the extended part of the protein, this method enables for example the analysis of the molecular weight of the protein, its cellular location, post-translational modifications or interactions with other factors without requiring the presence of protein-specific antibodies.

An advantage of viral epitopes compared to cellular epitopes is that these protein sequences do not usually occur in bacterial and eukaryotic proteins and thus no cross-reactions would be expected in bacterial or cellular systems.

A viral epitope frequently described in the literature that is used for such analyses is derived from the haemagglutinin of the human influenza virus. This epitope has the amino acid sequence YPYDVPDYA (98-106) (SEQ ID NO: 1) (Field, J. et al. (1988), Mol. Cell. Biol. Vol. 8, No. 5, 2159-2165 and Wilson et al., Cell 37, 767-778, (1984)). Monoclonal antibodies (mAB) against this epitope have been described and are available such as for example the mAB 12CA5 (P. A. Kolodziej and Young, R. A., Meth. Enzymol. (1991), Vol. 194, 508-519; Chen, Y. -T. et al. (1993), Proc. Natl. Acad. Sci., Vol. 90, 6508-6512)) and the anti-HA-BabCo.

However, a disadvantage of these antibodies is that their affinity is not high enough and therefore the epitope-specific antibodies have to be used in a high concentration for a sensitive detection of the corresponding fusion proteins which can lead to unspecific interactions which for example become apparent as cross-reactions in a Western blot (cf. Chen et al., p. 6510).

The inadequate affinity also leads to a lower sensitivity of the known anti-HA mAB.

Therefore the object of the invention was to provide monoclonal antibodies against the viral epitope YPYDVPDYA (SEQ ID NO: 1) which have a higher affinity and which are thus suitable for highly sensitive haemagglutinin tests or HA fusion protein tests and give reproducible results.

According to the invention monoclonal antibodies are provided which recognize the epitope having the amino acid sequence YPYDVPDYA (98-106) (SEQ ID NO: 1) of the haemagglutinin of the human influenza virus as well as corresponding fragments thereof and have an affinity of $>10^8$ $M^{-1}$, in particular of $10^9$ to $10^{10}$ $M^{-1}$. In this connection epitope fragments are understood in particular as those amino acid sequences which correspond to at least 70% of the sequence YPYDVPDYA (SEQ ID NO: 1) or are shortened by at least one to two terminal amino acids.

In order to produce the monoclonal antibodies, small mammals, preferably rats, such as e.g. Lou/C rats or mice such as e.g. BalbC mice or rabbits are immunized with a HA peptide synthesized by standard methods. An uncoupled HA peptide or a HA peptide which is optionally coupled N-terminally or C-terminally to a carrier protein or a HA fusion protein is used as the antigen. Keyhole limpet haemocyanin (KLH) or bovine serum albumin (BSA) were preferably used as carrier proteins. Subsequently B lymphocytes were isolated from the spleen of the animals and immortalized by cell fusion with suitable myeloma cells or by other known methods such as e.g. by means of oncogenes (Jonak, Z. L. et.al., (1988) Adv. Drug Rev. 2:207-228) or in an electrical field (Zimmermann, U. (1982). Biochim. Biophys. Acta 694:227-277). The cell fusion was preferably carried out according to the invention with spleen cells of Lou/C rats and myeloma cells from the mouse line P3x63-Ag8,653 (Kearney, J. F. et al (1979), J. Immunol. 123, 1548-1550).

In this process the lymphocytes and the myeloma cells are fused by known methods, in particular by polyethylene glycol fusion (PEG), virus fusion or electrofusion and the hybrid cells (cell clones) that are formed are also selected by known methods such as e.g. by using selection media.

Thus for example positive clones were firstly tested with HA peptides and then with HA fusion proteins. In a first screen a biotinylated HA peptide e.g. Bio-C-HA (acetyl-YPYDVPDYAGSGSK (ϵ-biotinoyl)-amide) (SEQ ID NO: 2) or Bio-N-HA (biotinoyl-ϵ-Aca-SGSGYPYDVPDYA-amide) (SEQ ID NO: 3) was used and a HA-tagged glutathione-S-transferase (GST) was used in a second screen. Clones that were again positive were subsequently examined with regard to their affinity with the aid of plasmon resonance in a BIACORE® (registered trademark of Biacore AB) system and they were selected.

The hybrid cells were cloned, cultured and multiplied according to known methods and optionally stored in liquid nitrogen.

The cell lines R 3F10, R 3A12 and R 6D12 were established as the most active cell clones with a stable antibody production. The hybridoma R 3A12 was deposited on the 08.10.1996 at the "Deutsche Sammlung für Mikroorganismen und Zellkulturen (DSMZ)", Mascheroder Weg 1b, 38124 Braunschweig under the number DSM ACC2286.

For the antibody isolation the hybrid cells were further propagated in cell culture or optionally in vivo by transplantation as ascites tumours. The mABs were isolated from the cell culture supernatants or optionally from the ascites fluid of the tumour-carrying experimental animals.

The mAB produced in high concentration by the hybrid cells which are characterized by an excellent specificity and binding strength for the YPYDVPDYA (SEQ ID NO: 1) epitope of the haemagglutinin of the human influenza virus or for corresponding epitope fragments are obtained according to the invention. They enable the highly sensitive detection and isolation of haemagglutinin as well as of proteins to which the HA epitope YPYDVPDYA (SEQ ID NO: 1) has been attached.

The affinity of the mAB according to the invention is $>10^8$ $M^{-1}$. Thus the affinity of the mAB 3F10 at $10^{10}$ $M^{-1}$ is approximately 30-fold higher than that of the known antibodies 12CA5 ($10^8$ $M^{-1}$) and BabCo ($10^7$ $M^{-1}$). The affinity of the mABs 3A12 and 6D12 according to the invention is $10^9$ $M^{-1}$ and is thus also higher than that of the known antibodies. The mABs according to the invention can be used in much lower concentrations and cross-reactions can be almost completely ruled out. They enable an improved sensitivity of the detection. It has turned out that they recognize native HA of the influenza virus, modified HA as well as HA fusion proteins. Hence they can be used very well for the determination of proteins in known detection reactions such as e.g. a solid phase two-side binding test.

Figure legends

FIG. 1:

Affinities of the mABs according to the invention compared to the mAB 12CA5 and anti-HA BabCo.

FIG. 2:

Immunoblot analysis of a HA-modified glutathione-S-transferase protein with a mAB (clone 3F10) according to the invention and anti-HA of the prior art (clone 12CA5); a) detection with anti-rat-peroxidase, b) anti-rat biotin/streptavidin-peroxidase.

FIG. 3:

Immunoblot analysis of a HA-modified glutathione-S-transferase protein with a mAB (clone 3F10) according to the invention and anti-HA of the prior art (clone 12CA5).

FIG. 4:

Immunoblot analysis of a HA-modified glutathione-S-transferase protein with enzyme (peroxidase) conjugates of an antibody according to the invention (clone 3F10) and an antibody of the prior art (clone 12CA5).

FIG. 5:

Immunoprecipitation of a HA-modified green fluorescent (GFP-HA) protein with a mAB (clone 3F10) according to the invention and anti-HA of the prior art (clone 12CA5).

Subsequently the invention is further elucidated by the following examples of use.

Example 1

Production of Clones R 3F10, R 3A12 and R 6D12

HA peptide preparation

The following peptides were synthesized:

Bio-C-HA (acetyl-YPYDVPDYAGSGSK (ε-biotinoyl)-amide) (SEQ ID NO: 2)

Bio-N-HA (biotinoyl-ε-Aca-SGSGYPYDVPDYA-amide) (SEQ ID NO: 3)

KLH-MPS-CUZU-HA-C

KLH-MPS-CUSU-HA-N

Immunization of small mammals

Lou/C rats were immunized intraperitoneally with KLH-coupled HA peptide according to the following scheme:

For the primary immunization the animals were injected with 50 μl KLH-coupled HA peptide in complete Freund's adjuvant.

Further immunizations were carried out with 50 μg KLH-coupled HA peptide in incomplete Freund's adjuvant.

Fusion

The subsequent fusion of the spleen cells of the Lou/C rats was carried out using mouse P3x63-Ag8,653 in the presence of PEG according to Krammer et al (1990) Hybridoma 9, 309-317.

Selecting the clones

Screening scheme:

1st Screen

An SA-coated microtitre plate (MTP) was coated with 1 μg/ml Bio-C-HA or Bio-N-HA, hybridoma supernatants were used undiluted and added to the coated MTP, the bound antibodies were detected with the aid of anti-rat-POD conjugate/TMB substrate.

2nd Screen

A maxisorb MTP was coated with HA-tagged GST (1 μl/ml in carbonate buffer), the hybridoma supernatants selected in the 1st screen were again used undiluted and added to the coated MTP, the bound antibodies were detected with the aid of anti-rat-POD conjugate/TMB substrate.

3rd/4th Screen

BIACORE® measurements were carried out with an analogous coating.

Result 5 clones with the highest affinity and the longest half-time of dissociation were selected with the aid of plasmon resonance in the BIACORE® system. They were named R 3F10, R 3A12, R 6D12, R 4H10 and M5B9. The affinity was only slightly different depending on the biotinoylated position of the peptides (C-terminus of N-terminus cf. FIG. 1).

The clones R 3F10, R 3A12 and R 6D12 were established as cell lines. They exhibit a good growth and a stable antibody production, and the antibodies that are produced have a 10-fold to 100-fold higher affinity than the monoclonal antibodies of the prior art 12CA5 and anti-HA BabCo.

FIG. 1 shows the affinities of the mABs according to the invention compared to the mAB 12CA5 and anti-HA BabCo.

Example 2

Determination of the Affinity Constants as well as of the Rate Constants of Association and Dissociation of the Antibodies that are Produced The affinity constants and rate constants of association and dissociation of the antibodies that were produced was determined with BIACORE® from the Pharmacia Biosensor Company (BIA stands for Biospecific Interaction Analysis). The measurement principle is based on surface plasmon resonance. The measurement is carried out on a biosensor, the so-called sensor chip. The biotinylated peptide is coupled to the streptavidin coated sensor chip by means of a non-covalent, high affinity bond. A solution of the antibody to be examined is passed over the sensor chip in the process of which the antibody is bound to the immobilized peptide by means of non-covalent forces of interaction.

The binding of the individual components increases the mass density on the surface of the sensor chip which is converted by the instrument into a proportional measurement signal. The rate constants of association and dissociation and, derived therefrom, the affinity constants can be calculated from the change in the signal versus time, the sensorgram.

The antibody-peptide complexes can be detached again with simple agents without impairing the peptides bound to the surface so that additional binding experiments can be carried out on the same sensor chip under identical boundary conditions.

In order to couple the biotinylated peptides to the sensor chip (SA, Pharmacia Biosensor) a solution containing a concentration of 50 mmol/l in HBS (10 mmol/l HEPES, 150 mmol/l NaCl, 3,4 mmol/l EDTA, 0.05% P20 pH 7.4) is passed over the sensor chip at a flow rate of 5 ml/min.

Afterwards the antibodies are added in HBS and binding to the peptides is monitored at a flow rate of 10 μl/min. The rate constants of association and dissociation of the binding of the antibody to the peptides are calculated from the sensorgrams with the aid of the manufacturer's software (BIA evaluation 2.1, Pharmacia Biosensor). The affinity constants are calculated from Ka=kon/koff. The values determined in this manner for the antibodies according to the invention to Bio-C-HA and BioN-HA as antigens are summarized in Table 1.

TABLE 1

| anti-HA-mAB | Antigen | kon l/mol*s | koff l/s | Ka l/mol |
|---|---|---|---|---|
| Babco | Bio-C-HA | 9.5 E +3 | 1.0 E −3 | 9.3 E +6 |
| 12CA5 | Bio-C-HA | 2.3 E +4 | 2.6 E −4 | 9.2 E +7 |
| R3F10 | Bio-C-HA | 5.9 E +5 | 4.8 E −5 | 1.2 E +10 |
| R3A12 | Bio-C-HA | 1.7 E +5 | 5.4 E −4 | 3.1 E +8 |
| R6D12 | Bio-C-HA | 4.0 E +5 | 7.6 E −5 | 5.2 E +9 |
| Babco | Bio-N-HA | 1.2 E +4 | 5.0 E −4 | 2.3 E +7 |
| 12CA5 | Bio-N-HA | 5.3 E +4 | 2.1 E −4 | 2.6 E +8 |
| R3F10 | Bio-N-HA | 6.2 E +5 | 9.1 E −5 | 6.8 E +9 |
| R3A12 | Bio-N-HA | 7.7 E +5 | 1.4 E −4 | 5.7 E +9 |
| R6D12 | Bio-N-HA | 5.9 E +5 | 1-2 E −4 | 5.1 E +9 |

Example 3

Comparative Immunoblot Analysis of a HA-modified Protein Using an Antibody According to the Invention and an Antibody Known from the Prior Art 3.1 Variation of the antigen Glutathione-S-transferase modified with the HA epitope (GST-HA) was serially diluted to the stated amounts, separated by means of SDS polyacrylamide gel electrophoresis and, after transfer onto a nylon membrane, reacted with the stated antibodies at the stated concentrations of the primary antibodies (1 μg/ml clone 12CA5; 0.1 μg/ml clone 3F10; Western blot analysis). Bound anti-HA antibodies were subsequently detected using anti-mouse-peroxidase (in the case of clone 12CA5), anti-rat-peroxidase (in the case of clone 3F10, a)) or anti-rat-biotin/streptavidin peroxidase (in the case of clone 3F 10, b)) and by chemiluminescence detection.

SDS polyacrylamide gel electrophoresis

8×7 cm gels with a thickness of 0.75 mm were used (BIO-RAD, Mini-Protean II™). For a 15% gel, 6 ml separation gel solution (1×) was poured between the plates. The top edge of the separation gel was carefully covered with a layer of 1 ml water. After 30 min polymerisation, the water was removed and it was filled with 2 ml collection gel solution (1×). The samples were mixed with 1 volume of two-fold concentrated Laemmli buffer, incubated for 10 min at 60° C. and pipetted into the rinsed gel pockets. The electrophoresis was carried out in mobile buffer at a current strength of ca. 15 mA.

Solutions:

4× separation gel solution:
1.5 M Tris/HCl, pH 8.8
0.4% SDS
4× collection gel solution:
0.5 M Tris/HCl, pH 6.8
0.4% SDS
2× Laemmli buffer:
1.52 g Tris per 100 ml
10 ml glycerol pH 6.8 adjusted with 1 N HCl
2.0 g SDS
2.0 ml 2-mercaptoethanol
1 mg bromophenol blue
5× mobile buffer:
15.1 g Tris per 1 1
72.0 g glycine
5.0 g SDS Transfer onto nylon membrane After the electrophoretic separation of the protein samples, a nylon filter corresponding to the gel size and moistened with $H_2O$ was placed on the gel. To ensure better contact two correctly cut Whatman® 3 MM papers were placed on each of the two sides and the construction was clamped in a BIO-RAD electroblot apparatus. After filling the chamber with transfer buffer, the proteins were transferred onto the membrane by applying a voltage of 70 V (current strength, I=250-350 mA) for 45-60 min while cooling on ice and stirring.

Solution:

transfer buffer: 25 mM Tris/HCl, pH 8.3 192 mM glycine

Detection

After carefully removing the membrane, the filter was incubated for 60 min at RT in PBS solution to which 1% blocking reagent (PBS/PR; Boehringer Mannheim) has been added in order to saturate binding sites that are still free. It was washed twice for 10 min in PBS buffer containing 0.1% Tween 20 (PBST) and reacted for 60 min at RT with the corresponding anti-HA antibody in the stated concentrations. After washing three times in PBST buffer (5 min each time, RT), the filters were incubated for a further 60 min at room temperature with an anti-species IgG-peroxidase conjugate (anti-rat-peroxidase, 20 mU/ml PBS/BR; anti-mouse-peroxidase, 40 mU/ml PBS/BR). It was washed again as described above and the filter membrane was incubated for 1 min in a 1:100 mixture of detection reagent A+B (Boehringer Mannheim) after removing the buffer with an absorbent cloth, and adhering reagent was removed. Subsequently an X-ray film was exposed for 1-10 min with the filters covered with a household foil.

Result

Figure 2:
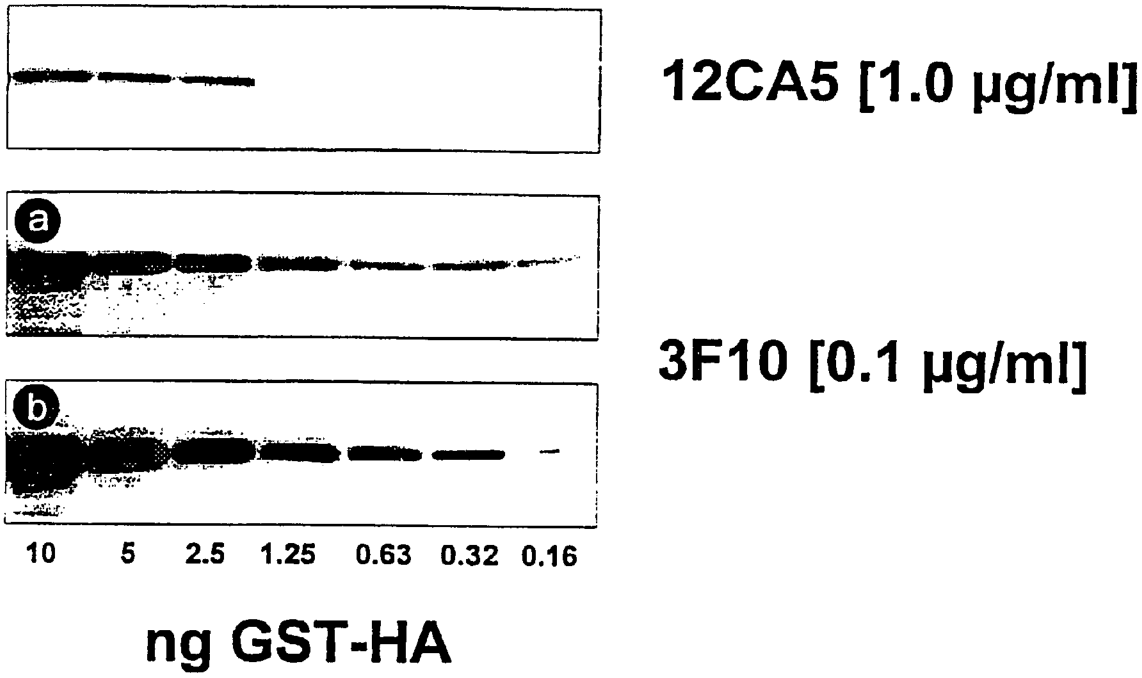

Using a ca. 10-fold lower antibody concentration, it is possible to detect a 30-fold lower amount of GST-HA using the antibodies according to the invention such as clone 3F10 compared to known antibodies such as clone 12CA5 (FIG. 2).

3.2 Variation of the concentration of the primary antibody 4 ng of the glutathione-S-transferase modified with the HA epitope (GST-HA) was separated in each lane by means of SDS polyacrylamide gel electrophoresis and, after transfer onto a nylon membrane, reacted with the stated antibodies in the stated concentrations of the primary antibodies (clone 12CA5 and 3F10; 2.0-0.008 ng/ml). Bound anti-HA antibodies were subsequently detected using anti-mouseperoxidase (in the case of clone 12CA5) and anti-rat-peroxidase (in the case of clone 3F10) and by chemiluminescence detection.

SDS polyacrylamide gel electrophoresis, transfer onto a nylon membrane and subsequent detection were carried out as described in example 3.1

Figure 3:
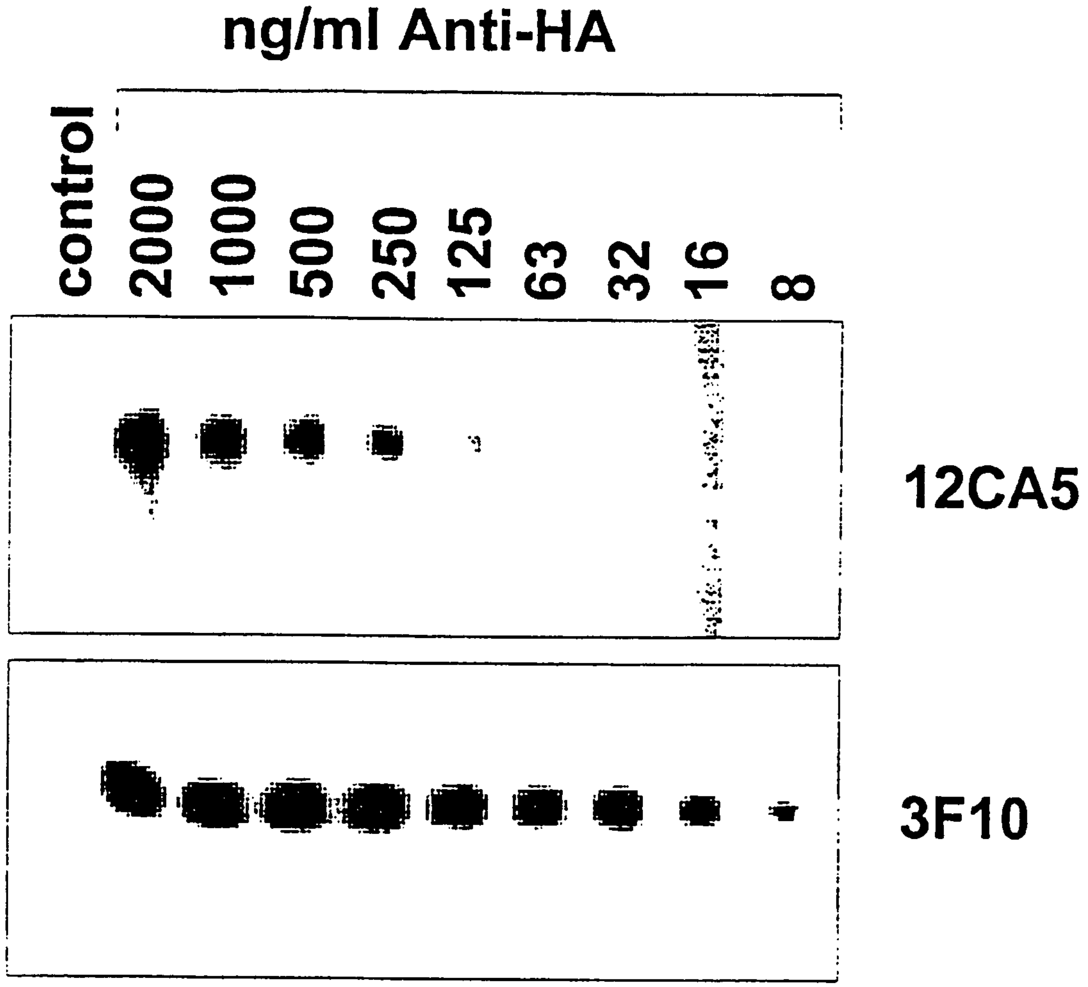

Result:

In the described experiment clone 12CA5 (prior art) becomes the limiting factor at an antibody concentration of ≦2000 ng/ml whereas at an antibody concentration of ca. 125 ng/ml signal saturation is observed with the clone 3F10 according to the invention (FIG. 3).

Comparable signals are obtained in the case of clone 3F10 at ca. 20-fold lower antibody concentrations.

Example 4

Comparable Immunoblot Analysis of a HA-modified Protein Using Antibody Conjugates Glutathione-S-transferase modified with the HA epitope (GST-HA) was serially diluted to the stated amounts, separated by means of SDS polyacrylamide gel electro-phoresis and, after transfer onto a nylon membrane, reacted with the aid of the stated antibody-peroxidase conjugates at the stated concentrations (100 ng/ml (clone 12CA5); 20 mU/ml (clone 3F10)). Bound anti-HA antibodies were subsequently detected using chemiluminescence detection.

SDS polyacrylamide gel electrophoresis, transfer onto a nylon membrane and subsequent detection were carried out as described in example 3.1.

Figure 4:
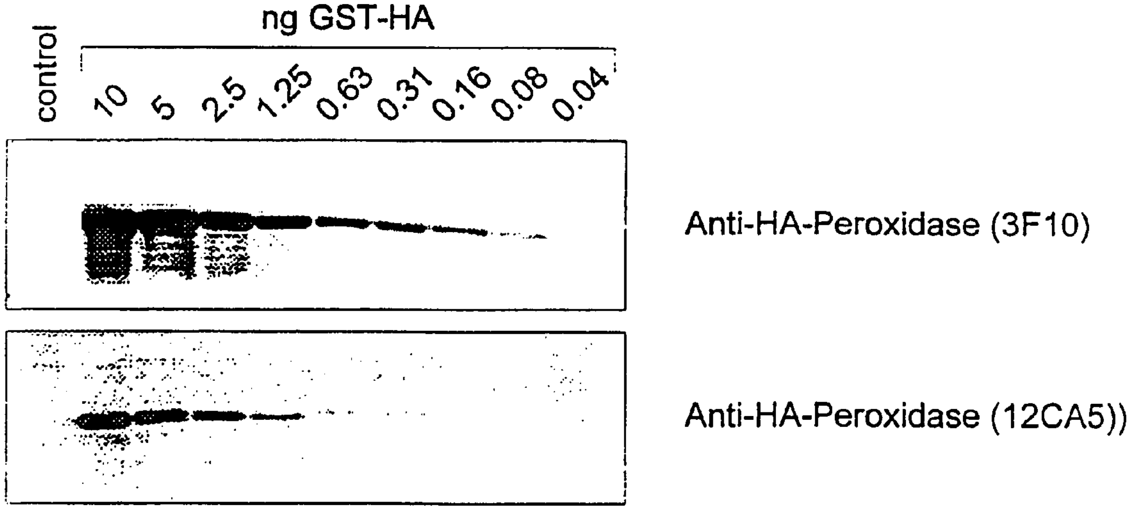

Result:

The detection limit in this system for the peroxidase conjugate of the clone 12CA5 (prior art) is ca. 1 ng GST-HA whereas 40 pg GST-HA can still be detected under the same conditions with the corresponding derivative of the clone 3F10 (FIG. 4).

Example 5

Comparative Immunoprecipitation of a HA-modified Protein

Green-fluorescent protein modified with the HA epitope (GFP-HA) was reacted with the stated amounts [in μg] of anti-HA antibodies (clone 12CA5 and clone 3F10) and immunoprecipitated after adding protein-G-agarose. The precipitates obtained were solubilized, separated by means of SDS polyacrylamide gel electrophoresis and, after transfer onto a nylon membrane, detected with an anti-HA-peroxidase conjugate (clone 12CA5) and by chemiluminescence detection.

Immunoprecipitation 50 ng of the green-fluorescent protein modified with the HA epitope (GFP-HA) was diluted in 200 μl wash buffer, the stated amounts of anti-HA antibody were added and it was incubated for 1 h at 4° C. in an overhead shaker. 25 μl of a 50% protein-G-Sepharose suspension was then added to the mixture and it was again incubated for 1 h as before. Proteins bound to the gel matrix via protein G were washed three times with 1 ml wash buffer and in each wash step the mixture was incubated for 2 min at 4° C. as described above. Thefmixture was then centrifuged for 2 min in a bench centrifuge (15,000 rpm, RT) and the pellet was taken up in 10 ml 1× Laemmli application buffer. The immunoprecipitated proteins were subsequently separated by denaturing gel electrophoresis (SDS polyacrylamide gel).

SDS polyacrylamide gel electrophoresis, transfer onto a nylon membrane and subsequent detection were carried out as described in example 3.1.

Figure 5:
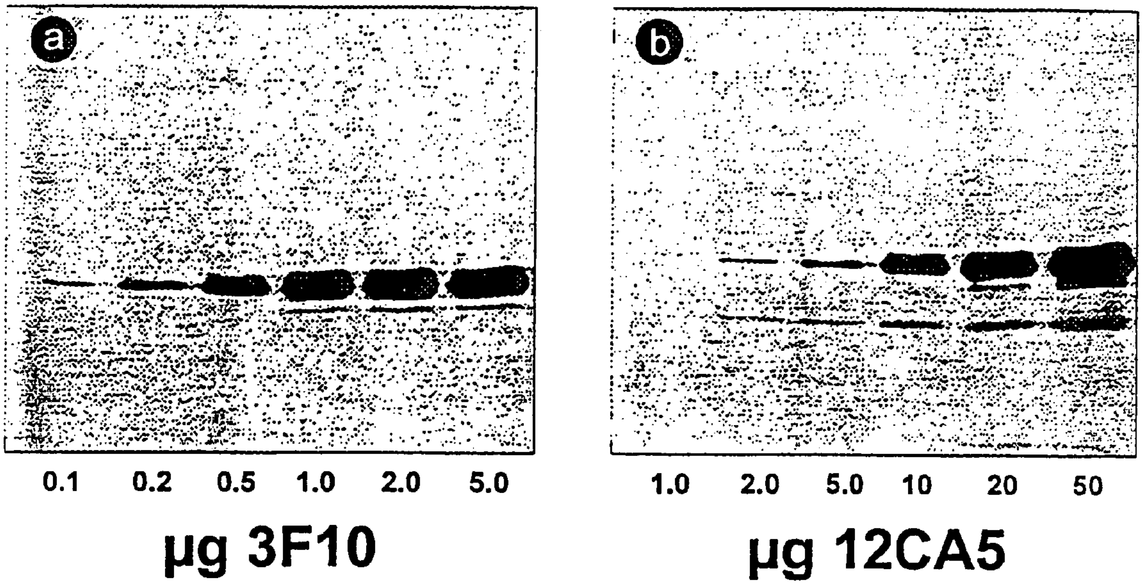

Result:

Compared to the clone 12CA5 (prior art) the clone 3F10 is able in the described experiment to precipitate the antigen used with a ≦20-fold lower antibody quantity (FIG. 5).

What is claimed is:

1. The monoclonal antibody produced by hybridoma R 3A12 deposited at the "Deutsche Sammlung für Mikroorganismen und Zellkulturen" under Accession No. DSM ACC2286 (08.10.1996).

2. A method for the production of a monoclonal antibody with binding specificity for the epitope YPYDVPDYA (SEQ ID NO: 1) comprising:

(a) providing a haemagglutinin peptide consisting of 13 or 14 amino acids, wherein a nine amino acid sequence of said epitope consists of the amino acid sequence YPYDVPDYA (SEQ ID NO: 1);

(b) immunizing a small mammal mammal with said peptide, (c) isolating B lymphocytes from the spleen of said mammal and fusing said lymphocytes with mouse myeloma cells to form clones, (d) selecting clones formed in step (c) that produce an antibody which binds to the haemagglutinin peptide and to a haemagglutinin fusion protein, and (e) selecting a clone from those selected in step (d) that produces and antibody with a binding affinity of $>10^8M^{-1}$ for the sequence YPYDVPDYA (SEQ ID NO: 1) and establishing said clone as a hybrid cell line.

3. The method of claim 2, wherein said haemagglutinin peptide is selected from the group consisting of acetyl-YPYDVPDYAGSGSK (ϵ-biotinoyl) amide (a derivative of SEQ ID NO: 2) and biotinoyl-ϵ-Aca-SGSGYPYDVPDYA amide (a derivative of SEQ ID NO: 3).

4. The method of claim 2, wherein said haemagglutinin fusion protein is haemagglutinin-tagged glutathione-S-transferase.

5. An isolated monoclonal antibody having a binding affinity of $>3\times10^8M^{-1}$ for an epitope consisting of acetyl-YPYDVPDYAGSGSK (ϵ-biotinoyl) amide (a derivative of SEQ ID NO: 2) or biotinoyl-ϵ-Aca-SGSGYPYDVPDYA amide (a derivative of SEQ ID NO: 3), as determined using a surface plasmon resonance system.

6. The monoclonal antibody of claim 5, wherein the antibody has a binding affinity of about 10° to about $10^{10}M^{-1}$.

* * * * *

UNITED STATES PATENT AND TRADEMARK OFFICE

CERTIFICATE OF CORRECTION

PATENT NO. : 7,255,859 B1
APPLICATION NO. : 09/284787
DATED : August 14, 2007
INVENTOR(S) : Emrich et al.

It is certified that error appears in the above-identified patent and that said Letters Patent is hereby corrected as shown below:

In the Claims:

Column 9, claim 2(b), line 52: Please delete “mammal mammal” and insert -- mammal -- therefor.

Column 9, claim 2(d), line 61: Please delete “and antibody” and insert -- an antibody -- therefor.

Column 10, claim 6, line 58: Please delete “$10^0$” and insert --$10^9$ -- therefor.

Signed and Sealed this

Thirteenth Day of November, 2007

JON W. DUDAS
*Director of the United States Patent and Trademark Office*